United States Patent

Ogasawara et al.

(10) Patent No.: US 6,437,133 B1
(45) Date of Patent: Aug. 20, 2002

(54) METHOD OF CATALYTICALLY REMOVING A PROTECTIVE GROUP CONTAINING AN ALLYL GROUP USING A REDUCING AGENT

(75) Inventors: Kunio Ogasawara; Takahiko Taniguchi, both of Sendai (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/554,246

(22) PCT Filed: Nov. 9, 1998

(86) PCT No.: PCT/JP98/05029

§ 371 (c)(1),
(2), (4) Date: May 11, 2000

(87) PCT Pub. No.: WO99/24381

PCT Pub. Date: May 20, 1999

(30) Foreign Application Priority Data

Nov. 11, 1997 (JP) .............................................. 9-325222

(51) Int. Cl.[7] .................... C07D 207/323; C07D 233/58
(52) U.S. Cl. .................... 546/143; 548/335.1; 548/439; 548/446; 548/564; 548/469; 549/448; 549/435; 564/90; 564/373; 564/374; 564/184; 564/218; 568/662; 568/675; 568/715
(58) Field of Search .............................. 548/335.1, 439, 548/564

(56) References Cited

FOREIGN PATENT DOCUMENTS

| JP | 08-053412 | 2/1996 |
|---|---|---|
| JP | 08508896 | 9/1996 |
| JP | 08325167 | 12/1996 |

OTHER PUBLICATIONS

Akiyama et al., "AlCl$_3$–N,N–Dimethylaniline: A new Benzyl and Allyl–Ether Cleavage Reagent", *Tetrahedron Letters*, vol. 32, No. 10, pp. 1321–1324, (1991).

Espanet et al., "SmCl$_3$–Catalyzed Electrochemical Cleavage of Allyl Ethers", *Tetrahedron Letters*, vol. 33, No. 18, pp. 2485–2488, (1992).

Nakayama et al., "A Useful Method for Deprotection of the Protective Allyl Group at the Anomeric Oxygen of Carbohydrate Moieties Using Tetrakis (triphenylphosphine) palladium", *Chem. Pharm. Bull.*, vol. 40, No. 7, pp. 1718–1720. (1992).

Ito et al., "Practical Zirconium–Mediated Deprotective Method of Allyl Groups", *J. Org. Chem.*, vol. 58, pp. 774–775, (1993).

Beugelmans et al., "Reductive Deprotective of Aryl Allyl Ethers with Pd(Ph3)4/NABH4", vol. 35, No. 25, pp. 4349–4350, (1994).

*Primary Examiner*—Robert W. Ramsuer
(74) *Attorney, Agent, or Firm*—Browdy and Neimark

(57) ABSTRACT

A method of efficiently removing the protective group from a protected hydroxyl or amino group with an allyl derivative by one step reaction under neutral conditions.

A protected hydroxyl or amino group is converted into a free hydroxyl or amino group in one-step by adding a reducing agent to an allyl derivative in the presence of nickel dichlorobis (diphenylphospino) propane.

6 Claims, No Drawings

METHOD OF CATALYTICALLY REMOVING A PROTECTIVE GROUP CONTAINING AN ALLYL GROUP USING A REDUCING AGENT

The present application is the national stage under 35 U.S.C. §371 of International Application PCT/JP98/05029, filed Nov. 9, 1998, which designated the United States, and was not published in English.

TECHNICAL FIELD

The present invention relates to a method of removal of protective group with an allyl group, which is useful for protecting hydroxyl groups or amino groups in a process for producing several kinds of organic compounds such as pharmaceuticals, agricultural chemicals, natural organic compounds or liquid crystal compounds.

BACKGROUND ART

When a hydroxyl group or an amino group of organic compound is protected, an allyl group is very useful skeleton as protection group under wide reaction conditions such as acidic or basic condtions. Generally, a method for changing the group protected with an allyl group into a hydroxyl group or an amino group (namely, a deprotecting method) consists of two steps, in which the allyl group is changed into an enol ether structure or enamine structure by isomerization with a transition metal such as rhodium or under basic conditions and then hydrolyzed with an acid in the presence of a mercury salt. Although the allyl group can be used as a protecting group, the utilization is limited by such an inconvenient deprotecting method.

In recent years, some deprotecting methods of one step has been reported (Akiyama et al., Tetrahedron Letters, 1991, 32, 1321-1324; Espane et al, Tetrahedron Letters, 1992, 33, 2485-2488; Nakayama et al., Chem. Pharm. Bull., 1992, 40, 1718-1720; Ito et al., J. Org. Chem., 1993, 58, 774-775; Boujerman, Tetrahedron Letters, 1994, 35, 4349-4350), and these methods are, however, impractical for technical production. The methods are limited because these are inapplicable to compounds having substituent groups or skeletons unstable under acid conditions.

The present invention aims to provide a reaction method for easily proceeding in one step under mild conditions and for changing the group protected with an allyl group into a hydroxy group or an amino group.

DISCLOSURE OF THE INVENTION

The present inventors have widely investigated to resolve the above problems, and have found that an allyl derivative represented by a general formula (1):

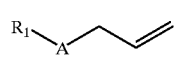
(1)

wherein $R_1$ shows an organic residue; A shows an oxygen atom or $-NR_2$; and $R_2$ shows a hydrogen atom or a organic residue, is treated with a reductant in the presence of nickel dichlorobis (diphenylphosphino) propane to obtain a compound represented by a general formula (2):

(2)

wherein $R_1$ shows an organic residue; A shows an oxygen atom or $-NR_2$; and $R_2$ shows a hydrogen atom or an organic residue, to complete the present invention.

BEST MODE FOR CARRYING OUR THE INVENTION

As a starting material of the compound represented by general formula (1) for applying the method of the present invention, organic compounds having hydroxy groups or amino groups can be used without any limitation. Precursors or derivatives such as terpenes, steroids, sugars, indols, agrycone parts in macrolides, prostaglandins, and quinolones can be concretely exemplified.

These starting materials and allylhalides are treated under basic conditions to easily obtain the componds (allyl derivatives) represented by general formula (1). The other usable methods of allylation are Gyve et al., Tetrahedron Letters, 22, 3591 (1981), Satoh et al., Tetrahedron Letters, 29, 4097 (1988), Racmili et al., Tetrahedron Letters, 30, 4669 (1989), and Aniszarman et al., Carbohydr. Res., 174 (1988).

Thus obtained allyl groups are used as protection groups, desired skeletons are introduced from the starting materials via several kinds of reaction, and these groups can be changed into hydroxy groups or amino groups by the deprotecting method of the present invention.

An allyl derivative is dissolved in a solvent, nickel dichloro (diphenylphospino) propane ((dppp)NiCl$_2$) of 1-5 mol % based on the allyl derivative is added, and the mixture is stirred. As the solvent, any solvent dissolvable the allyl derivative can be used. Diethylether, tetrahydrofuran (THF), toluene, dichloroethane, and a THF/ethanol mixed solvent can be preferably exemplified.

Diisobutylaluminum hydride, sodium borohydride, or trialkylaluminum of 1.0-1.5 equivalent (preferably 1.5 equivalent) based on the allyl derivative is added slowly to the solution in an atmosphere of argon or nitrogen at a temperature of −10-40° C. (preferably 0-5° C.). Although diisobutylaluminum hydride or trialkylaluminum may be neat, solvent such as toluene, hexane, heptane, cyclohexane, THF, or dichloromethane may be added to dissolve it. Sodium borohydride may be used as powder, or suspension with THF/ethanol mixed solvent.

The mixture is stirred at the same temperature for 5-10 minutes, and more at 10-40° C. for 2-10 hours. The reaction solution is then diluted, water is added and the mixture is stirred for 1-2 hours. The solid material is filtered off with a filter aid such as cerite, and the solvent is distilled away. The resulting residue is subjected to common operation such as column chromatography or recrystallization to obtain a purified compound represented by general formula (2).

EXAMPLES

The present invention is more concretely described by examples in the following. However, the present invention is not limited by these examples.

Example 1

Deprotection of 1-allyloxy-4-methoxybenzene 1-allyloxy-4-methoxybenzene (100 mg, 0.6mmol) and nickel dichlorobis (diphenylphosphino) propane (3mg, 6 μmol) were dissolved in diethyl ether (2 ml), and the mixture was cooled to 0° C. A 1.5M toluene solution of diisobutyl aluminum hydride (600 μl, 0.9 mmol) was added to the mixture under an atmosphere of argon, and the mixture was stirred at the same temperature for 5 minutes. The reaction solution was warmed to room temperature and stirred for 2 hours. The solution was diluted by adding diethyl ether (3 ml), water (600 μl) was added thereto, and the mixture was stirred for further 1 hour.

After the reaction solution was dried over anhydrous magnesium sulfate, cerite was added thereto, the mixture was filtered, and the solvent was distilled away from the filtrate in vacuo. The resultant residue was subjected to silica gel chromatography (elution solvent: diethyl ether/hexane= 1/1) to obtain 4-methoxyphenol (68 mg, yield 90%).

Examples 2-8

Using several kinds of allyl ether, deprotection reactions were carried out according to Example 1 and the results are shown in Table 1.

TABLE 1

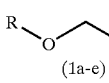

| Ex. | Allyl ether | R | solvent | hour | product | Yield(%) |
|---|---|---|---|---|---|---|
| 2 | 1a | 4-MeOC$_6$H$_4$- | CH$_2$Cl$_2$ | 2 | 2a | 86 |
| 3 | 1a | Ditto | THF | 2 | 2a | 88 |
| 4 | 1a | Ditto | Et$_2$O | 2 | 2a | 90 |
| 5 | 1b | PhCH$_2$CH$_2$ | Et$_2$O | 2 | 2b | 85 |
| 6 | 1c | 1-menthyl | Et$_2$O | 3 | 2c | 97 |
| 7 | 1d | Choresteryl | Et$_2$O | 2 | 2d | 95 |
| 8 | 1e | 1-adamantyl | Et$_2$O | 3 | 2e | 80 |

Example 9

The same procedure as in Example 1 was repeated except that diisobutyl aluminum hydride of reductant was changed into boron sodium hydride (1.5 eqivalent), and diethyl ether of solvent was changed into a THF/ethanol (4/1) mixture solution, and 4-methoxyphenol (62mg, yield 82%) was obtained.

Examples 10-15, 19 and 20

Using several kinds of allyl ether, deprotection reactions were carried out according to Example 1, and the results are shown in Table 2. In the table, Ph shows a phenyl group, and Bn shows a benzyl group.

Examples 16-18

Using several kinds of allyl ether, deprotection reactions were carried out according to Example 9, and the results are shown in Table 2.

TABLE 2

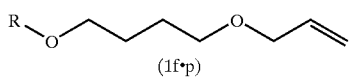

| Ex. No. | Allyl ether | R | Solvent | Hour | Product | Yield (%) |
|---|---|---|---|---|---|---|
| 10 | 1f | tert-Bu(Me)2Si- | Et$_2$O | 2 | 2f | 92 |
| 11 | 1g | MeOCH2- | Et$_2$O | 2 | 2g | 90 |
| 12 | 1h | THP- | Et$_2$O | 2 | 2h | 89 |
| 13 | 1i | 4-MeOC6H4- | Et$_2$O | 2 | 2i | 95 |
| 14 | 1j | benzyl- | Et$_2$O | 2 | 2j | 95 |
| 15 | 1k | prenyl- | Et$_2$O | 2 | 2k | 80 |
| 16 | 1l | acetyl- | THF-EtOH (4:1) | 2 | 2l | 73 |
| 17 | 1m | pivaloyl- | THF-EtOH (4:1) | 2 | 2m | 85 |
| 18 | 1n | benzoyl- | THF-EtOH (4:1) | 2 | 2n | 80 |
| 19 | 1o | 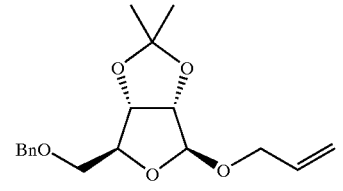 | Et$_2$O | 2 | 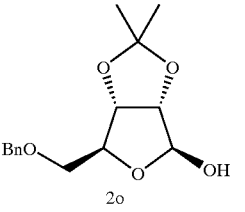 2o | 45 |
| 20 | 1p | 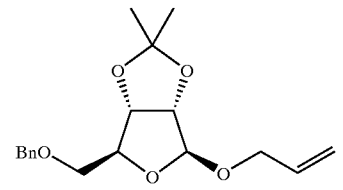 | Et$_2$O | 2 | 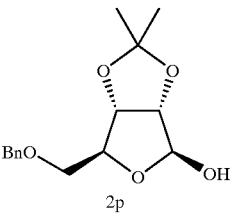 2p | 56 |

Examples 21 and 22

Using several kinds of allyl ether, deprotection reactions were carried out according to Example 1, and the results are shown in Table 3.

TABLE 3

BnO~~~~O~~~~ (1q) → [DIBAL / (dppp)NiCl₂] → BnO~~~~OH (2q)

| Ex. No. | Allyl ether | Structure | Solvent | Reaction time (hr) | Product | Yield (%) |
|---|---|---|---|---|---|---|
| 21 | 1q | BnO~~~O~~~ | Et₂O | 2 | BnO~~~OH | 71 |
| 22 | 1r | (cyclohexene with OAllyl, OBn, OBn, OBn) | Et₂O | 1 | 2r (cyclohexene with OH, OBn, OBn, OBn) | 93 |

Examples 23-27

Using several kinds of allyl ether, deprotection reactions were carried out according to Example 1, and the results are shown in Table 4.

TABLE 4

(1s–u) → [DIBAL / (dppp)NiCl₂] → (2s–u)

| Ex. No. | Allyl ether | Structure | Solvent | Reaction time (hr) | DIBAL (equiv.) | Product | Yield (%) |
|---|---|---|---|---|---|---|---|
| 23 | 1s | 1,2-bis(allyloxy)benzene | Et₂O | 2 | 1.3 | 2s | 37 |
| 24 | 1t | 1,3-bis(allyloxy)benzene | Et₂O | 2 | 1.3 | 2t | 41 |
| 25 | 1u | 1,4-bis(allyloxy)benzene | Et₂O | 2 | 1.3 | 2u | 56 |

TABLE 4-continued

[Reaction scheme: (1s-u) → (2s-u) with DIBAL / (dppp)NiCl₂]

| Ex. No. | Allyl ether | Structure | Solvent | Reaction time (hr) | DIBAL (equiv.) | Product | Yield (%) |
|---|---|---|---|---|---|---|---|
| 26 | 1v | [CH₂=CHCH₂-O-(CH₂)₄-O-CH₂CH=CH₂] | Et₂O | 2 | 1.3 | [CH₂=CHCH₂-O-(CH₂)₄-OH] 2v | 58 |
| 27 | 1w | [structure shown] | Et₂O | 2 | 1.3 | [structure shown] 2w | 9 |

Example 28

Diisobutyl alminum hydride (1.5M toluene solution, 689 ml, 1.0 mmol) was added to an anhydrous toluene solution (2 ml) of N-allyl-methylaniline (100 mg, 680 mmol) and nickel dichloro bis (diphenyl phosphino) propane (15 mg, 27 mmol) under ice cooling, and the mixture was stirred for one hour at room temperature. After the reaction, diethyl ether (3 ml) and a 0.5N solution (680 ml) of sodium hydroxide were added under ice cooling, and the mixture was stirred at room temperature for one hour. The reaction solution was dried over anhydrous magnesium sulfate, cerite was added thereto, the mixture was filtered, and the solvent was distilled away from the filtrate in vacuo. The resulting residue was subjected to silica gel chromatography (elution solution: diethyl ether/n-hexane=1/5, v/v) to obtain N-methylaniline (66 mg, yield 91%).

Example 29

Trimetyl alminum (0.98M n-hexane solution, 1.3 ml, 1.3 mmol) was added to an anhydrous toluene solution (2 ml) of N-allyl-N-benzoyl aniline (100 mg, 422 mmol) and nickel dichloro bis (diphenyl phosphino) propane (9 mg, 17 mmol) under ice cooling, and the mixture was refluxed for 7 hours. After the reaction, diethyl ether (3 ml) and a 0.5N solution (1.3 ml) of sodium hydroxide were added under ice cooling, and the mixture was stirred at room temperature for 2 hours. The reaction solution was dried over anhydrous magnesium sulfate, cerite was added thereto, the mixture was filtered, and the solvent was distilled away from the filtrate in vacuo. The resulting residue was subjected to silica gel chromatography (elution solution: diethyl ether/n-hexane=1/5, v/v) to N-benzoyl aniline (61 mg, yield 73%).

Examples 30-42

Using several kinds of allyl ether, deprotection reactions were carried out according to Example 28, and the results are shown in Table 5.

TABLE 5

[Reaction: $R_1R_2N$-allyl → $R_1R_2NH$ with DIBAL (1.5–2.5 equiv.) / (dppp)NiCl₂]

| Ex | $R_1$ | $R_2$ | Yield (%) |
|---|---|---|---|
| 30 | O-Benzyl-2-prolinol | | 69 |
| 31 | PhCH₂CH₂ | PhCH₂ | 87 |
| 32 | PhCH₂ | Me | 84 |
| 33 | PhCH₂ | PhCH₂ | 82 |
| 34 | 1,2,3,4-tetrahydroisoquinoline | | 90 |
| 35 | PhCH₂ | (Me)₂C=CHCH₂ | 77 |
| 36 | Ph | (Me)₂C=CHCH₂ | 80 |
| 37 | Ph | CH₂=CHCH₂ | 79 |
| 38 | Ph | PhCH₂ | 80 |
| 39 | Ph | PhCH₂ | 71 |
| 40 | PhCH₂CH₂ | H | 69 |
| 41 | PhCH₂ | H | 66 |
| 42 | Ph | H | 79 |

Examples 43-47

Using several kinds of allyl derivatives having a five-membered ring skeleton, deprotection reactions were carried out according to Example 28. The results are shown in Table 6.

TABLE 6

| Ex. No. | Starting material | Product | Yield (%) |
|---------|-------------------|---------|-----------|
| 43 | N-allyl pyrrole | pyrrole (NH) | 38 |
| 44 | N-allyl imidazole | imidazole (NH) | 81 |
| 45 | N-allyl indole | indole (NH) | 72 |
| 46 | N-allyl tetrahydrocarbazole | tetrahydrocarbazole (NH) | 81 |
| 47 | N-allyl carbazole | carbazole (NH) | 71 |

Examples 48-51

Using several kinds of allyl derivatives, deprotection reactions were carried our according to Example 28. The results are shown in Table 7.

TABLE 7

$$\text{Tol-SO}_2\text{-N(R}_2\text{)-CH}_2\text{CH=CH}_2 \xrightarrow[\text{(dppp)NiCl}_2]{\text{DIBAL (1.5-2.5 equiv.)}} \text{Tol-SO}_2\text{-NH-R}_2$$

| Ex. | $R_2$ | Yield (%) |
|-----|-------|-----------|
| 48 | PhCH$_2$CH$_2$ | 93 |
| 49 | PhCH$_2$ | 89 |
| 50 | Ph | 95 |
| 51 | H | 81 |

Examples 52-57

Using several kinds of allyl derivatives, deprotection reactions were carried out according to Example 29. The resulte are shown in Table 8.

TABLE 8

| Ex. | $R_1$ | $R_2$ | Yield (%) |
|---|---|---|---|
| 52 | Me | PhCH$_2$CH$_2$ | 57 |
| 53 | Me | PhCH$_2$ | 51 |
| 54 | Me | Ph | 54 |
| 55 | Ph | PhCH$_2$CH$_2$ | 78 |
| 56 | Ph | PhCH$_2$ | 70 |
| 57 | Ph | 4-MeOPh CH$_2$ | 92 |
| 58 | Ph | 4-MeOPh | 78 |

Industrial Applicability

Using the present invention, it is possible to provide a deprotection method of allyl groups. The process proceeds efficiently in one step under neutral conditions.

What is claimed is:

1. A method for catalytically removing a protective group containing an allyl group, comprising reacting an allyl compound represented by formula (1):

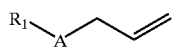 (1)

wherein $R_1$ is an organic group; A is an oxygen atom or —$NR_2$; and $R_2$ is a hydrogen atom or an organic group, with a reducing agent in the presence of nickel dichlorobis (diphenylphosphino) propane to obtain a compound represented by formula (2):

$$R_1\text{—AH.} \quad (2)$$

2. The method of claim 1, in which the reducing agent is diisobutyl aluminum hydride.

3. The method of claim 1, in which the reducing agent is sodium borohydride.

4. The method of claim 1, in which the reducing agent is trialkyl aluminum.

5. The method of claim 1, in which $R_1$ is alkyl, aryl, aralkyl, alkenyl, alkynyl, monocycloalkyl, bicycloalkyl, tricycloalkyl, monocycloaryl, bicycloaryl, tricycloaryl, heteroalkyl or a hetero ring.

6. The method of claim 1, in which A is —$NR_2$ and $R_2$ is alkyl, aryl, aralkyl, alkenyl, monocycloalkyl, bicycloalkyl, tricycloalkyl, heteroalkyl, monocycloaryl, bicycloaryl, tricyloaryl, alkylsulfonyl, arylcarbonyl or arylsulfonyl.

* * * * *